United States Patent
Cunkle et al.

[11] Patent Number: 6,117,276
[45] Date of Patent: Sep. 12, 2000

[54] INHIBITING POLYMERIZATION OF VINYL AROMATIC MONOMERS

[75] Inventors: Glen T. Cunkle, Stamford, Conn.; Thomas F. Thompson, Yonkers, N.Y.; Volker H. von Ahn, Mahopac, N.Y.; Roland A. E. Winter, Armonk, N.Y.

[73] Assignee: Nalco/Exxon Energy Chemicals, L.P., Sugar Land, Tex.

[21] Appl. No.: 09/048,822

[22] Filed: Mar. 26, 1998

Related U.S. Application Data

[63] Continuation-in-part of application No. 08/755,875, Dec. 2, 1996, abandoned.

[51] Int. Cl.[7] ................. B01D 3/34; C07C 7/20
[52] U.S. Cl. ................... 203/8; 203/9; 203/57; 526/83; 526/84; 585/5
[58] Field of Search ............ 203/8, 9, 57, DIG. 11; 585/4, 5, 24; 526/83, 84

[56] References Cited

U.S. PATENT DOCUMENTS

| | | |
|---|---|---|
| 3,733,326 | 5/1973 | Murayama et al. . |
| 3,988,212 | 10/1976 | Watson . |
| 4,040,912 | 8/1977 | Watson . |
| 4,086,147 | 4/1978 | Watson . |
| 4,105,506 | 8/1978 | Watson . |
| 4,132,602 | 1/1979 | Watson . |
| 4,132,603 | 1/1979 | Watson . |
| 4,252,615 | 2/1981 | Watson . |
| 4,341,600 | 7/1982 | Watson . |
| 4,466,904 | 8/1984 | Watson et al. . |
| 4,468,343 | 8/1984 | Butler et al. . |
| 5,254,760 | 10/1993 | Winter et al. . |
| 5,545,782 | 8/1996 | Winter et al. ................. 585/5 |
| 5,616,774 | 4/1997 | Evans et al. ................. 585/4 |
| 5,877,344 | 3/1999 | Gande et al. .............. 560/205 |
| 5,910,232 | 6/1999 | Hyde et al. ................. 203/9 |
| 5,922,244 | 7/1999 | Koch et al. ............... 252/403 |

FOREIGN PATENT DOCUMENTS

| | | |
|---|---|---|
| 0240297 | 10/1987 | European Pat. Off. . |
| 1165534 | 6/1989 | Japan . |
| 1027150 | 10/1981 | U.S.S.R. . |
| 1139722 | 4/1983 | U.S.S.R. . |
| 1558888 | 12/1987 | U.S.S.R. . |
| 9616921 | 6/1996 | WIPO . |

OTHER PUBLICATIONS

Die Markromolekulare Chemie 160 (1972) 243–249 Miura, et al.
Golf'Fien, et al. Translated in Polymer Science (USSR) 1975 A 17(8,1919).
Polymer Bulletin 1982, 6,589 by G. Moad, et al.

*Primary Examiner*—Virginia Manoharan
*Attorney, Agent, or Firm*—Michael B. Martin; Thomas M. Breininger

[57] ABSTRACT

When a nitroxyl compound is heated in an oxygen-free atmosphere with a vinyl aromatic monomer at 50–140° C. for up to 60 days, it forms an activated inhibitor mixture which is superior to the nitroxyl compound itself in preventing the premature polymerization of a vinyl aromatic monomer during its processing and purification.

7 Claims, No Drawings

6,117,276

INHIBITING POLYMERIZATION OF VINYL AROMATIC MONOMERS

This is a continuation-in-part of application Ser. No. 08/755,875, filed on Dec. 2, 1996, now abandoned.

The instant invention pertains to an activated inhibitor composition and a process for reducing the premature polymerization of readily polymerizable vinyl aromatic monomers during the manufacturing and purification processes for preparing said monomers in pure form.

BACKGROUND OF THE INVENTION

Vinyl aromatic monomers, such as styrene, divinylbenzene and the like, produced by conventional processes contain byproducts and impurities. These undesired impurities must be removed from the desired monomer by separation and purification processes such as distillation in order for the monomer be suitable for further industrial applications. The elevated temperatures encountered during distillation causes thermal polymerization and formation of unwanted polymer. The polymer formation can be reduced by the use of a polymerization inhibitor.

In a typical purification process, the impure vinyl aromatic monomer to be distilled is mixed with a polymerization inhibitor before being subjected to distillation conditions in the distillation system. However, a significant amount of undesired polymer is often formed in the distillation system which substantially reduces the yield of high purity monomer obtained as well as causing severe and costly operational difficulties in the purification process. Still worse, occasionally, complete premature polymerization of the vinyl aromatic monomer occurs causing considerable economic loss. A typical distillation system is described in detail in U.S. Pat. Nos. 4,252,615 and 4,341,600, the relevant parts of which are incorporated herein by reference.

To prevent premature polymerization of vinyl aromatic monomers during the distillation purification process, various compounds have been used as polymerization inhibitors. Sulfur was widely employed in the past for this purpose. However, more recently, a number of organic compounds have been disclosed and used as substitutes for sulfur as polymerization inhibitors for such monomers with mixed success.

U.S. Pat. No. 4,086,147 discloses 2-nitro-p-cresol as a polymerization inhibitor. U.S. Pat. Nos. 4,105,506 and 4,252,615 disclose 2,6-dinitro-p-cresol as such a polymerization inhibitor. U.S. Pat. Nos. 4,132,602 and 4,132,603 disclose the use of a halogenated aromatic nitro compound as a polymerization inhibitor for use during the distillation of vinyl aromatic compounds. However, in each of these cases, the organic compounds have relatively weak activity and must be used at fairly high concentrations for any significant inhibition activity especially when higher distillation temperatures are involved. Additionally, the relatively high toxicity of these aromatic nitro compounds makes them far from attractive as a practical solution to the premature polymerization problem encountered with vinyl aromatic monomers during their purification and distillation.

U.S. Pat. Nos. 3,988,212 and 4,341,600 disclose the use of N-nitroso-diphenylamine combined with dinitrocresol derivatives for inhibiting the polymerization of vinyl aromatic compounds under vacuum distillation conditions. U.S. Pat. No. 4,466,904 discloses the use of phenothiazine, 4-tert-butylcatechol and 2,6-dinitro-p-cresol as a polymerization inhibitor system in the presence of oxygen during heating of a vinyl aromatic monomer. U.S. Pat. No. 4,468,343 discloses the use of 2,6-dinitro-p-cresol and either a phenylenediamine or 4-tert-butylcatechol in the presence of oxygen to prevent premature polymerization of vinyl aromatic compounds during heating. European patent application EP 0240297 A1 teaches the use of a substituted hydroxylamine and a dinitrophenol to inhibit the premature polymerization of a vinyl aromatic compound at elevated temperatures as during distillation. However, in each of these cases the effectiveness of the polymerization inhibitor mixture is oxygen dependent. This results in inconsistent inhibition due to a variable and unpredictable distribution of air (oxygen) throughout the distillation system. Additionally, there is the greatly increased possible explosion safety hazard which may occur because of the presence of air in the system. It is clear that there still exists a great need for a stable polymerization inhibitor system of relatively low toxicity which will effectively and safely prevent the premature polymerization of vinyl aromatic compounds during distillation particularly in the absence of oxygen (air).

U.S. Pat. No. 3,733,326 discloses the polymerization inhibition of vinyl monomers by use of free radical precursors. Soviet Patent No. 1,027,150 teaches the stabilization of styrene by using a nitroxyl radical. Soviet Patent No. 1,139,722 discloses the use of a bis-nitroxyl compound as a thermal polymerization inhibitor for styrene. Japanese Hei 1-165534 teaches the use of 1-piperidyloxy derivatives as polymerization inhibitors for styrene. Soviet Patent No. 1,558,888 discloses the polymerization inhibition of styrene by a nitroxyl radical. The inhibition of styrene polymerization by selected hindered amine nitroxyl derivatives is also discussed by Y. Miura et al., Makro mol. Chem. 1972, 160, 243; by M. D. Golf'fein et al., Vysokomol. soyed 1975, A17 (8), 1671 translated in Polymer Science (USSR), 1975, A17 (8), 1919; and by G. Moad et al., Polymer Bull. 1982, 6, 589. The Moad reference teaches the use of 1-oxyl-2,2,6,6-tetramethylpiperidine and 2-oxyl-1,1,3,3-tetramethylisoindoline, but do not suggest that the mixtures prepared in their experimental section are per se useful as an inhibitor when added to fresh styrene or any other aromatic vinyl monomer to prevent the premature polymerization of said monomer. U.S. Pat. No. 5,254,760 discloses the use of stable hindered nitroxyl compounds combined with aromatic nitro compounds to prevent premature polymerization of vinyl aromatic compounds during distillation and purification processes.

OBJECTS OF THE INVENTION

One object of the invention is to provide a method for enhancing the effectiveness of nitroxide compounds in the inhibition of polymerization of vinyl aromatic monomers.

Another object of the invention is to provide a process for inhibiting the premature polymerization of vinyl aromatic monomers during their distillation or purification which comprises incorporating therein an effective inhibiting amount of a mixture of activated hindered nitroxyl compound with the proviso that the nitroxyl compound is neither 1-oxyl-2,2,6,6-tetramethylpiperidine nor 2-oxyl-1,1,3,3-tetramethylisoindoline.

DETAILED DESCRIPTION OF THE INVENTION

The instant invention pertains to a method for enhancing the effectiveness of stable hindered nitroxides for preventing the premature polymerization of vinyl aromatic compounds during distillation and purification by preparation of an activated nitroxyl-vinyl aromatic monomer mixture which is superior to the nitroxyl compound itself in preventing the premature polymerization of vinyl aromatic monomers.

More specifically, the instant activated nitroxyl-vinyl aromatic monomer mixture, which is capable of enhanced inhibition of the premature polymerization of vinyl aromatic monomers, is the product prepared by heating, under an oxygen-free atmosphere, a mixture of 0.1 to 50% by weight of a stable hindered nitroxyl compound and 99.9 to 50% by weight of a vinyl aromatic compound at 50–140° C. for 0.5 hours to 60 days with the proviso that the nitroxyl compound is neither 1-oxyl-2,2,6,6-tetramethylpiperidine nor 2-oxyl-1,1,3,3-tetramethylisoindoline.

Preferably, the instant activated mixture is prepared by heating, under an oxygen-free atmosphere, a mixture of 1 to 20% by weight of a stable hindered nitroxyl compound and 99 to 80% by weight of a vinyl aromatic compound at 90–130° C. for 2 to 100 hours; most preferably for 2 to 50 hours.

Surprisingly, the activated mixture described above is much more effective at preventing polymerization of a vinyl aromatic monomer than is a mixture of the same components, but which mixture has not been heated by the instant process.

The vinyl aromatic monomers which are useful in the instant process include styrene, divinylbenzene and structural isomers, 4-styrenesulfonic acid and mixtures thereof. Preferably, the vinyl aromatic monomer is styrene.

The stable hindered nitroxyl compound useful in this invention has the generic structure

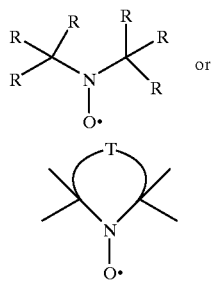

where each R is alkyl and T is a group required to complete a 5- or 6-membered ring.

Two or more nitroxyl groups may also be present in the same molecule

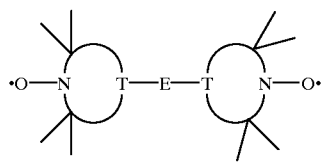

by being linked through the T moiety by a linking group E.

Preferably, the stable hindered nitroxyl compound is selected from the group consisting of
1-oxyl-2,2,6,6-tetramethylpiperidin-4-ol,
1-oxyl-2,2,6,6-tetramethylpiperidin-4-one,
4-n-propoxy-1-oxyl-2,2,6,6-tetramethylpiperidine,
1-oxyl-2,2,6,6-tetramethylpiperidin-4-yl acetate,
1-oxyl-2,2,6,6-tetramethylpiperidin-4-yl butyrate,
1-oxyl-2,2,6,6-tetramethylpiperidin-4-yl 2-ethylhexanoate,
1-oxyl-2,2,6,6-tetramethylpiperidin-4-yl octanoate,
1-oxyl-2,2,6,6-tetramethylpiperidin-4-yl stearate,
1-oxyl-2,2,6,6-tetramethylpiperidin-4-yl benzoate,
1-oxyl-2,2,6,6-tetramethylpiperidin-4-yl 4-tert-butylbenzoate,
bis(1-oxyl-2,2,6,6-tetramethylpiperidin-4-yl) succinate,
bis(1-oxyl-2,2,6,6-tetramethylpiperidin-4-yl) adipate,
bis(1-oxyl-2,2,6,6-tetramethylpiperidin-4-yl) sebacate,
bis(1-oxyl-2,2,6,6-tetramethylpiperidin-4-yl) n-butylmalonate,
bis(1-oxyl-2,2,6,6-tetramethylpiperidin-4-yl) phthalate,
bis(1-oxyl-2,2,6,6-tetramethylpiperidin-4-yl) isophthalate,
bis(1-oxyl-2,2,6,6-tetramethylpiperidin-4-yl) terephthalate,
bis(1-oxyl-2,2,6,6-tetramethylpiperidin-4-yl) hexahydroterephthalate,
N,N'-bis(1-oxyl-2,2,6,6-tetramethylpiperidin-4-yl) adipamide,
N-(1-oxyl-2,2,6,6-tetramethylpiperidin-4-yl)acetamide,
N-1-oxyl-2,2,6,6-tetramethylpiperidin-4-yl-caprolactam,
N-1-oxyl-2,2,6,6-tetramethylpiperidin-4-yl-dodecylsuccinimide,
2-oxyl-1,1,3,3-tetraethylisoindoline,
2,4,6-tris-[N-butyl-N-(1-oxyl-2,2,6,6-tetramethylpiperidin-4-yl]-s-triazine,
4,4'-ethylenebis(1-oxyl-2,2,6,6-tetramethylpiperazin-3-one) and
di-tert-butyl nitroxyl.

When the activated inhibitor mixture of the instant invention is used for inhibiting the premature polymerization of fresh aromatic vinyl monomer, the activated inhibitor mixture is optionally the same as the mixtures prepared by Moad et al. from the nitroxyl compound 1-oxyl-2,2,6,6-tetramethylpiperidine or 2-oxyl-1,1,3,3-tetramethylisoindoline as well as those listed above as preferred nitroxyl compounds.

Most preferably, the nitroxyl compound is
bis(1-oxyl-2,2,6,6-tetramethylpiperidin-4-yl) sebacate,
N-(1-oxyl-2,2,6,6-tetramethylpiperidin-4-yl)acetamide,
1-oxyl-2,2,6,6-tetramethylpiperidin-4-ol, or
1-oxyl-2,2,6,6-tetramethylpiperidin-4-one.

The instant invention also pertains to a process for inhibiting the premature polymerization of a vinyl aromatic compound during distillation and purification which comprises incorporating in said vinyl aromatic compound an effective inhibiting amount of the activated nitroxyl-vinyl aromatic monomer mixture with the proviso that the nitroxyl compound is neither 1-oxyl-2,2,6,6-tetramethylpiperidine nor 2-oxyl-1,1,3,3-tetramethylisoindoline.

The effective inhibiting amount of the activated nitroxyl-vinyl aromatic mixture varies over wide ranges depending on the concentration of the nitroxyl compound in the mixture before activation by heating, the particular vinyl aromatic compound and the condition encountered in distillation of the monomer.

Normally, the vinyl aromatic compound is distilled or purified at temperatures from 50–15° C. The activated mixture is normally added to the vinyl aromatic compound continuously or intermittently upstream to the point where distillation or purification occurs.

Preferably, an amount of activated nitroxyl-vinyl aromatic monomer mixture is added to the vinyl aromatic monomer to be purified sufficient to achieve a 1 ppm to 2000 ppm of activated mixture, based on the weight of monomer being purified. For example, for a 10% nitroxyl in vinyl aromatic monomer mixture, 5000 ppm of the activated mixture will give 500 ppm of activated nitroxyl. For most application a range of 5 to 1000 ppm of activated nitroxyl is used. As the temperature of distillation rises, greater amounts of inhibitor are required. The activated polymerization inhibiting mixture of this invention is well suited for protecting the reboiler sections of a distillation column during distillation of vinyl aromatic monomers or the compressor sections before the monomer enters a distillation column.

The activated polymerization inhibitor mixtures can be introduced into the monomer to be protected by any conventional method. It may be added just upstream of the point of desired application by any suitable means. In addition, this mixture may be injected separately into the distillation train along with the incoming feed of monomer or through separate entry points providing efficient distribution of the activated inhibitor mixture. Since the inhibitor is gradually depleted during operation, it is generally necessary to maintain the appropriate amount of the activated inhibitor mixture in the distillation system by adding additional inhibitor during the course of the distillation process. Such addition may be carried out either on a continuous basis or by intermittently charging fresh inhibitor into the distillation system if the concentration of the inhibitor is to be maintained above the minimum required level.

This invention enables the distillation plant to operate more safely at an increased rate of production compared to prior art processes because of the greater effectiveness of the activated inhibitor mixture with or without the presence of oxygen (air) and thus to permit higher distillation temperatures with minimal polymer formation.

The following examples are meant to illustrate the instant invention and are not to be construed to limit the scope of the instant invention in any manner whatsoever.

In the following Examples, styrene is used as being representative of the vinyl aromatic monomers.

EXAMPLES 1–4

Commercial grade styrene is freed of the tert-butylcatechol storage stabilizer by washing with 1N aqueous sodium hydroxide followed by distillation under reduced pressure.

The activated inhibitor mixture of this invention is prepared as follows: A deoxygenated mixture of 1.0 g of bis(1-oxyl-2,2,6,6-tetramethylpiperidin-4-yl) sebacate and 11.5 g of styrene (purified as described above) is heated at 100° C. under a nitrogen atmosphere. Aliquots (2 mL) are removed after heating for 24 hours (Example 2), after 32 hours (Example 3) and after 48 hours (Example 4).

The relative effectiveness of the activated inhibitor mixture compared to pure nitroxyl compound is seen as follows below: A 300-mL three-necked flask equipped with a thermometer, condenser, rubber septum and magnetic stirrer bar is charged with 100 g of styrene (purified as described above) and 200 mg of bis(1-oxyl-2,2,6,6-tetramethylpiperidin-4-yl) sebacate (Example 1) or charged in separate experiments with 99.75 g of purified styrene and 0.25 g of the activated inhibitor mixture prepared above in Examples 2, 3 and 4. An oxygen-free atmosphere is established by five consecutive evacuations and backfilling with nitrogen, followed by sparging the styrene solution with pure nitrogen for 15 minutes. The vessel is immersed into a mechanically stirred and thermostatically controlled oilbath at 120° C. Small aliquots are removed periodically and analyzed for polymer content. The amount of polystyrene formed is then determined by refractive index measurements, calibrated with authenic polystyrene in styrene solutions of known concentrations. The results are shown in the table below.

| | Percent Polymer Formed after Heating | | |
|---|---|---|---|
| Example | 60 minutes | 75 minutes | 90 minutes |
| 1 | 3.5 | 5.5 | 7.7 |
| 2 | 1.1 | 2.1 | 3.5 |
| 3 | 0.5 | 1.4 | 2.7 |
| 4 | 0.3 | 0.6 | 1.6 |

It is clear from these data that each of the activated inhibitor mixtures of Examples 2, 3 and 4 provide superior inhibition efficacy to prevent or mitigate the premature polymerization of the styrene monomer than does the pure nitroxyl compound itself as seen in Example 1.

EXAMPLES 5–7

Commercial grade styrene is freed of the tert-butylcatechol storage stabilizer as described in Examples 1–4.

The activated inhibitor mixture of this invention is prepared as follows: A deoxygenated mixture of 1.0 g of 1-oxyl-2,2,6,6-tetramethylpiperidin-4-one and 11.5 g of styrene (purified as described above) is heated at 100° C. under a nitrogen atmosphere. Aliquots (2 mL) are removed after heating for 32 hours (Example 6) and after 48 hours (Example 7).

The relative effectiveness of the activated inhibitor mixture compared to pure nitroxyl compound is measured as described in Examples 1–4. In 100 g of styrene (purified as described above) is added 200 mg of 1-oxyl-2,2,6,6-tetramethylpiperidin-4-one 5) or charged in separate experiments with 99.75 g of purified styrene and 0.25 g of activated inhibitor mixture prepared above in Examples 6 and 7. Small aliquots are removed periodically and analyzed for polymer content. The amount of polystyrene formed is then determined by refractive index measurements, calibrated with authenic polystyrene in styrene solutions of known concentrations. The results are shown in the table below.

| | Percent Polymer Formed after Heating | | |
|---|---|---|---|
| Example | 60 minutes | 75 minutes | 90 minutes |
| 5 | 1.7 | 3.3 | 5.2 |
| 6 | 0.5 | 1.7 | 3.2 |
| 7 | 0.5 | 1.7 | 3.2 |

It is clear from these data that each of the activated inhibitor mixtures of Examples 6 and 7 provide superior inhibition efficacy to prevent or mitigate the premature polymerization of the styrene monomer than does the pure nitroxyl compound itself as seen in Example 5.

EXAMPLES 8–10

Commercial grade styrene is freed of the tert-butylcatechol storage stabilizer as described in Examples 1–4.

The activated inhibitor mixture of this invention is prepared as follows: A deoxygenated mixture of 1.0 g of 1-oxyl-2,2,6,6-tetramethylpiperidin-4-ol and 11.5 g of styrene (purified as described above) is heated at 100° C. under a nitrogen atmosphere. Aliquots (2 mL) are removed after heating for 32 hours (Example 9) and after 48 hours (Example 10).

The relative effectiveness of the activated inhibitor mixture compared to pure nitroxyl compound is measured as described in Examples 1–4. In 100 g of styrene (purified as described above) is added 200 mg of 1-oxyl-2,2,6,6-tetramethylpiperidin-4-ol (Example 8) or charged in separate experiments with 99.75 g of purified styrene and 0.25 g of the activated inhibitor mixture prepared above in Examples 9 and 10. Small aliquots are removed periodically and analyzed for polymer content. The amount of polystyrene formed is then determined by refractive index measurements, calibrated with authenic polystyrene in styrene solutions of known concentrations. The results are shown in the table below.

| | Percent Polymer Formed after Heating | | |
|---|---|---|---|
| Example | 60 minutes | 75 minutes | 90 minutes |
| 8 | 1.0 | 2.8 | 4.5 |
| 9 | 0.2 | 1.5 | 3.0 |
| 10 | 0.2 | 0.7 | 1.7 |

It is clear from these data that each of the activated inhibitor mixtures of Examples 9 and 10 provide superior inhibition efficacy to prevent or mitigate the premature polymerization of the styrene monomer than does the pure nitroxyl compound itself as seen in Example 6.

What is claimed is:

1. A process for inhibiting the premature polymerization of a vinyl aromatic compound during distillation and purification which consists essentially of
   incorporating in said vinyl aromatic compound an effective inhibiting amount of an activated nitroxyl-vinyl aromatic monomer mixture which is capable of inhibiting the premature polymerization of vinyl aromatic monomers, which is the mixture prepared by
   heating, under an oxygen-free atmosphere, a mixture of 0.1 to 50% by weight of a stable hindered nitroxyl compound

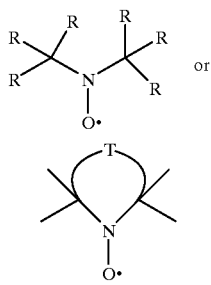

where each R is alkyl and T is a group required to complete a 5- or 6-membered ring, or

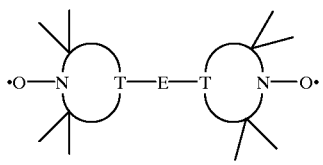

where two nitroxyl groups are linked through the T moiety by a linking group E, and 99.9 to 50% by weight of a vinyl aromatic compound at 50–140° C. for 0.5 hours to 60 days;

with the proviso that the nitroxyl compound is neither 1-oxyl-2,2,6,6-tetramethylpiperidine nor 2-oxyl-1,1,3,3-tetramethylisoindoline.

2. A process according to claim 1 wherein the vinyl aromatic compound is distilled or purified at temperatures from 50–150° C.

3. A process according to claim 1 wherein the activated mixture is incorporated in the vinyl aromatic compound continuously or intermittently upstream to the point where distillation or purification occurs.

4. A process according to claim 1 wherein the vinyl aromatic monomer is selected from the group consisting of styrene, divinylbenzene, 4-styrene-sulfonic acid and mixtures thereof.

5. A process according to claim 4 wherein the vinyl aromatic monomer is styrene.

6. A process according to claim 1 wherein the stable hindered nitroxyl compound is selected from the group consisting of
1-oxyl-2,2,6,6-tetramethylpiperidin-4-ol,
1-oxyl-2,2,6,6-tetramethylpiperidin-4-one,
4-n-propoxy-1-oxyl-2,2,6,6-tetramethylpiperidine,
1-oxyl-2,2,6,6-tetramethylpiperidin-4-yl acetate,
1-oxyl-2,2,6,6-tetramethylpiperidin-4-yl butyrate,
1-oxyl-2,2,6,6-tetramethylpiperidin-4-yl 2-ethylhexanoate,
1-oxyl-2,2,6,6-tetramethylpiperidin-4-yl octanoate,
1-oxyl-2,2,6,6-tetramethylpiperidin-4-yl stearate,
1-oxyl-2,2,6,6-tetramethylpiperidin-4-yl benzoate,
1-oxyl-2,2,6,6-tetramethylpiperidin-4-yl 4-tert-butylbenzoate,
bis(1-oxyl-2,2,6,6-tetramethylpiperidin-4-yl) succinate,
bis(1-oxyl-2,2,6,6-tetramethylpiperidin-4-yl) adipate,
bis(1-oxyl-2,2,6,6-tetramethylpiperidin-4-yl) sebacate,
bis(1-oxyl-2,2,6,6-tetramethylpiperidin-4-yl) n-butylmalonate,
bis(1-oxyl-2,2,6,6-tetramethylpiperidin-4-yl) phthalate,
bis(1-oxyl-2,2,6,6-tetramethylpiperidin-4-yl) isophthalate,
bis(1-oxyl-2,2,6,6-tetramethylpiperidin-4-yl) terephthalate,
bis(1-oxyl-2,2,6,6-tetramethylpiperidin-4-yl) hexahydroterephthalate,
N,N'-bis(1-oxyl-2,2,6,6-tetramethylpiperidin-4-yl) adipamide,
N-(1-oxyl-2,2,6,6-tetramethylpiperidin-4-yl)acetamide,
N-1-oxyl-2,2,6,6-tetramethylpiperidin-4-yl-caprolactam,
N-1-oxyl-2,2,6,6tetramethylpiperidin-4-yl-dodecylsuccinimide,
2-oxyl-1,1,3,3-tetraethylisoindoline,
2,4,6-tris-[N-butyl-N-(1-oxyl-2,2,6,6-tetramethylpiperidin-4-yl]-s-triazine,
4,4'-ethylenebis(1-oxyl-2,2,6,6-tetramethylpiperazin-3-one) and
di-tert-butyl nitroxyl.

7. A process according to claim 6 wherein the stable hindered nitroxyl compound is
bis(1-oxyl-2,2,6,6-tetramethylpiperidin-4-yl) sebacate,
N-(1-oxyl-2,2,6,6-tetramethylpiperidin-4-yl)acetamide,
1-oxyl-2,2,6,6-tetramethylpiperidin-4-ol, or
1-oxyl-2,2,6,6-tetramethylpiperidin-4-one.

* * * * *